United States Patent [19]

Beck

[11] Patent Number: 5,097,090
[45] Date of Patent: Mar. 17, 1992

[54] PROCESS FOR THE PREPARATION OF PERFLUOROALKYLETHYL ALCOHOLS

[75] Inventor: Leonard H. Beck, Wilmington, Del.

[73] Assignee: E. I. Du Pont de Nemours and Company, Wilmington, Del.

[21] Appl. No.: 530,351

[22] Filed: May 30, 1990

[51] Int. Cl.$^5$ ............................................. C07C 31/34
[52] U.S. Cl. ................................................. 568/842
[58] Field of Search ........................................ 568/842

[56] References Cited

U.S. PATENT DOCUMENTS 3,283,012  11/1966  Day ................................. 568/842

OTHER PUBLICATIONS

Chemical Engineering Handbook, 5th edition, Perry, Robert, McGraw Hill Book Company–1973, sections 6 and 21.

Primary Examiner—Alan Siegel
Assistant Examiner—Rebecca Cook

[57] ABSTRACT

In a process for the manufacture of 2-perfluoroalkylethyl alochols by sulfating 2-perfluoroalkylethyl iodides with oleum followed by hydrolysis of the resulting sulfated reaction mass with water, the improvement comprising carrying out both reactions in two similar continuous reactor systems, combined in series, in each of which one of the reactant streams is contacted with the reaction mass in a zone of intense agitation which forms part of a low volume recycle loop operated under pressure and at high rates of reecycle. Preferably the zone of intense agitation in the sulfation loop has an energy input of at least 0.05 horsepower per gallon per minute with a loop recycle time of 5 seconds or less, and the hydrolysis loop has an energy input of at least 0.4 horsepower per gallon per minute with a loop recycle time of 2 seconds or less. Most preferably, the energy input to the liquids in both loops is provided by centrifugal pumps.

4 Claims, 1 Drawing Sheet

PROCESS FOR THE PREPARATION OF PERFLUOROALKYLETHYL ALCOHOLS

FIELD OF INVENTION

This invention relates to an improved process for the conversion of 2-perfluoroalkylethyl iodides to 2-perfluoroalkylethyl alcohols by treatment with oleum followed by hydrolysis.

BACKGROUND OF THE INVENTION

A variety of methods are available for the manufacture of 2-perfluoroalkylethyl alcohols from 2-perfluoroalkylethyl iodides. Some methods suffer the disadvantages of using metallic catalysts and/or organic solvents, neither of which can be allowed to escape into the environment (U.S. Pat. No. 4,748,282, U.S. Pat. No. 478,760, U.S. Pat. No. 4,452,852, U.S. Pat. No. 4,001,309, U.S. Pat. No. 4,219,681 and DE 3016571). Others require the use of either expensive percarboxylic acids (U.S. Pat. No. 4,613,681) or refrigeration (DT 2628705). Still others afford only partial conversions or products of low purity (DT 18677, EP 245133A, J 55009025 and J 50047912).

While the method described by Day in U.S. Pat. No. 3,283,012, for the conversion of 2-perfluoroalkylethyl iodides to 2-perfluoroalkylethyl alcohols, does not suffer from the disadvantages cited above, it still is not without disadvantages of its own. Two main chemical reactions, sulfation and hydrolysis, take place in the manufacture of 2-perfluoroalkylethyl alcohols as described by Day. In the first, 2-perfluoroalkylethyl iodides are converted to 2-perfluoroalkylethyl pyrosulfates (described by Day as sulfates) by treatment with oleum. In the second, hydrolysis of the pyrosulfates results in the formation of the sulfates which, in turn, are converted to the desired 2-perfluoroalkylethyl alcohols. It is believed that, in the first step, an intermediate unstable sulfonyl iodide is formed which is then converted either to an alkyl pyrosulfate if contacted by additional sulfur trioxide, or to a bis-sulfate if no additional sulfur trioxide is immediately available. For this reason, an excess of oleum is used to minimize the formation of the bis sulfate which is undesirable because its rate of hydrolysis is much slower than that of the sulfate thus tending to increase its level, as well as the level of other impurities derived from it, in the product. No matter which reaction takes place, the main by-products of the reaction are elemental iodine and sulfur dioxide which react with water during the hydrolysis, to produce hydrogen iodide and sulfuric acid. The following is a representation, not intended to be limiting, of the various reactions (wherein R=RfCH2CH2):

Reaction 1) 2 RI + 2 SO$_3$ $\longrightarrow$ 2 ROSO$_2$I
 (iodide)          (sulfonyl idodide)

2) 2 ROSO$_2$I + SO$_3$ $\longrightarrow$ (ROSO$_2$)$_2$O + I$_2$ + SO$_2$
 (sulfonyl iodide)       (pyrosulfate)

3) 2 ROSO$_2$I $\longrightarrow$ (RO)$_2$SO$_2$ + I$_2$ + SO$_2$
 (sulfonyl idodide)    (bis-sulfate)

4) (RO)$_2$SO$_2$ + SO$_3$ $\longrightarrow$ (ROSO$_2$)$_2$O
 (bis sulfate)         (pyrosulfate)

-continued 5) (ROSO$_2$)$_2$O + H$_2$O $\longrightarrow$ 2 ROSO$_3$H
 (pyrosulfate)           (sulfate)

6) ROSO$_3$H + H$_2$O $\longrightarrow$ ROH + H$_2$SO$_4$
 (sulfate)            (alcohol)

7) (RO)$_2$SO$_2$ + 2 H$_2$O $\longrightarrow$ 2 ROH + H$_2$SO$_4$
 (bis-sulfate)           (alcohol)

8) I$_2$ + SO$_2$ + 2 H$_2$O $\longrightarrow$ 2HI + H$_2$SO$_4$ 9) (RO)$_2$SO$_2$ + ROH $\longrightarrow$ ROR + ROSO$_3$H
 (bis-sulfate) (alcohol)    (ether)  (sulfate)

10) (RO)$_2$SO$_2$ + HI $\longrightarrow$ RI + ROSO$_3$H
 (bis-sulfate)         (iodide) (sulfate)

When the first of the above reactions is carried out according to the procedures of Day, molten iodide is added to 65% oleum at 50°–55° C. over the course of 5–6 hours at atmospheric pressure. The reaction is vigorously exothermic. The temperature of the mass is controlled at 50°–55° C. during the addition to maintain most of the iodides as liquids, ready to react, thus preventing the build-up of solidified unreacted iodide which could lead to an uncontrollable condition, if, for some reason, all were to melt at one time and become available for reaction. During the addition of the molten iodide to the oleum, severe foaming occurs due to the viscous nature of the mass, the vigorously exothermic reaction, the formation of low-boiling by-product sulfur dioxide and the closeness of the reaction temperature to the boiling point of the sulfur trioxide in the oleum. The foaming, in turn, reduces the efficiency of the agitation leading to localized higher temperatures and deficencies in excess sulfur trioxide, both of which conditions favor increased undesirable bis sulfate formation. The foaming also reduces heat transfer efficency resulting in prolonged processing. Purer intermediate 2-perfluoroalkylethyl pyrosulfate would be obtained if the foaming could be avoided.

When the second main reaction, i.e., the hydrolysis, is carried out according to the methods of Day, the viscous sulfation mass, containing about 30–38% free sulfur trioxide, is added to water at atmospheric pressure with cooling. The reaction is so exothermic that it is violent. Splattering occurs at the surface, carrying insoluble materials into the scrubber. This condition is compounded by the formation of 2-perfluoroalkylethyl hydrate gels which form at the higher temperatures of the drowning. The gels rise in the mass, thereby reducing agitation at the surface and causing localized hot spots which lead to more severe splattering. The reduced agitation also results in intermittent thermal shocks which, in turn, have a deleterious effect on the glass-lined equipment. Vent losses and equipment failures could be avoided or minimized if a more controllable process were developed.

The problems associated with the sulfation and hydrolysis steps, were avoided in part by carrying out both reactions under pressure. Vent losses were reduced in both cases, but violent surface reactions were still experienced, especially in the case of the hydrolysis. In addition, serious safety concerns arose in connection with operating under pressure with large of quantities of such highly reactive chemicals.

BRIEF SUMMARY OF INVENTION

The present invention relates to an improvement in the known method of converting 2-perfluoroalkylethyl iodides to 2-perfluoroalkylethyl alcohols by treatment of the iodides with oleum followed by hydrolysis, the improvement comprising carrying out most of both reactions in two similar continuous reactor systems combined in series, in each of which the reactants are contacted in zones of intense agitation in low-volume loops operated under pressure and at high rates of recycle.

DETAILED DESCRIPTION OF THE INVENTION

Figure 1:
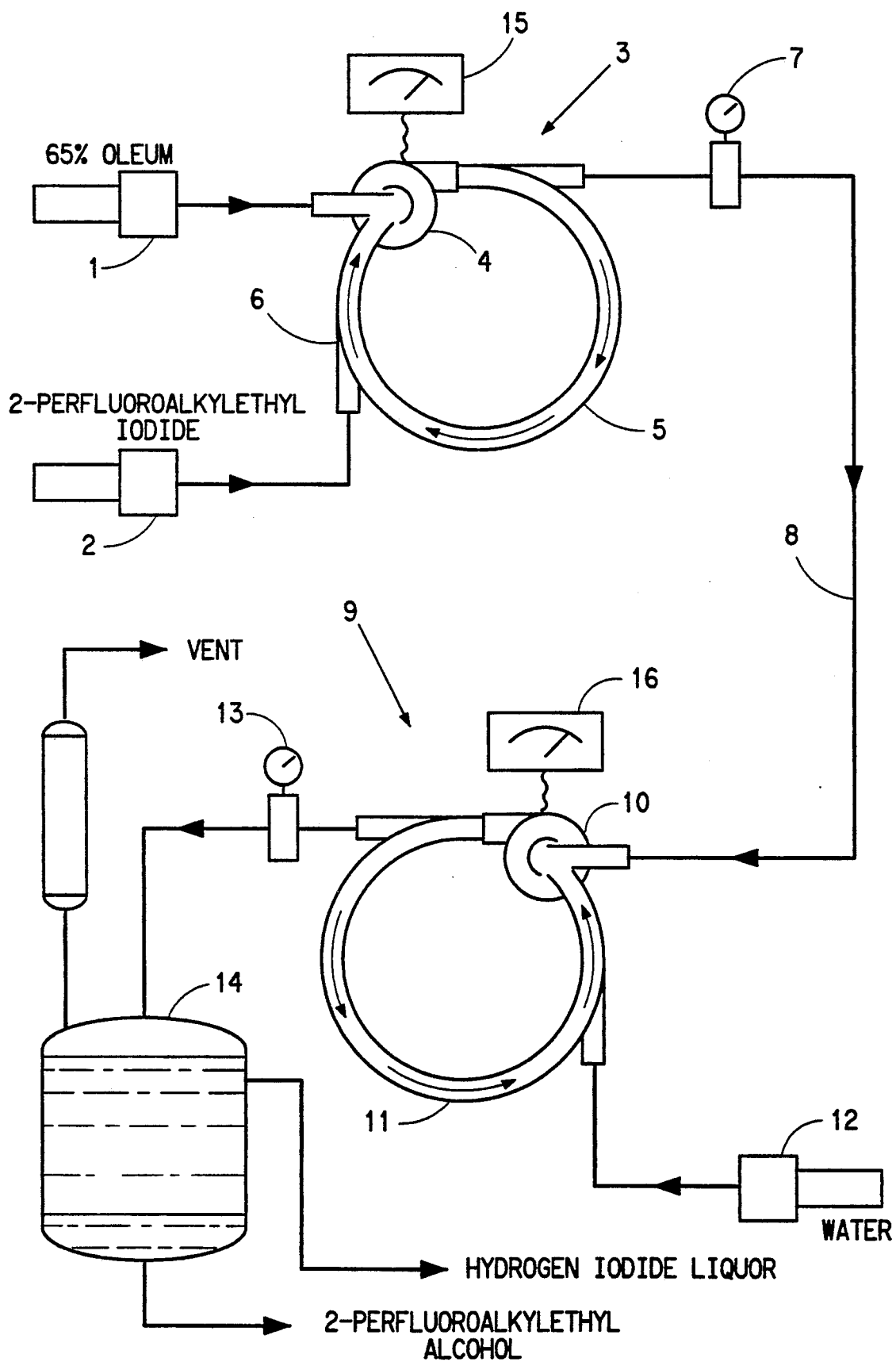

In accordance with the present invention, 2-perfluoroalkylethyl iodides are sulfated by treatment with oleum, followed by hydrolysis, effected by contacting the sulfation mass with water, to form the desired products, 2-perfluoroalkylethyl alcohols. Both reactions are carried out in similar ways in similar continuous reactor systems combined in series. In each reactor system, the reaction mass is recirculated rapidly in a low-volume loop containing a device which translates the energy input into high liquid shear and transport, or recycle, components, e.g., a centrifugal pump. In an embodiment of the invention, one reactant stream is introduced into the system by injection into the zone of intense agitation produced by the impeller of the centrifugal pump and the other reactant is charged into the mass at another part of the loop. Both reactor systems are run under pressure to prevent gasification of reactant sulfur trioxide and by-product sulfur dioxide thus avoiding foaming during processing. The above processing conditions afford improved control of the reactions, better quality product, less loss of valuable by-products and safer operation due to the low volumes of materials under pressure, as well as other benefits which will become apparent as the invention is further defined.

FIG. 1 illustrates the equipment used to operate a preferred embodiment of this invention. Pump 1 feeds 65% oleum and pump 2 feeds 2-perfluoroalkyl ethyl iodide to the sulfation loop 3 which is comprised of cenrifugal pump 4 and Teflon ® tubing 5. At steady state, the mass in loop 3 consists mostly of sulfated 2-perfluoroalkylethyl in excess oleum. On adding the oleum into the zone of intense agitation at the impeller of centrifugal pump 4, and adding the 2-perfluoroalkylethyl iodide into rapidly recirculating loop at 6, these two reactants quickly and quietly form the pyrosulfate (in direct contrast to the addition of the 2-perfluoroalkylethyl iodide to the oleum in the batch process in which splattering, foaming, poor mixing and thermal shocking of the equipment occur). The pressure in loop 3 is generated by pumps 1 and 2 and is controlled by the setting on pressure relief device 7 through which the reaction mass from loop is transferred via line 8 to the hydrolysis loop 9 comprised of centrifugal pump 10 and Teflon ® tubing 11. Water for the hydrolysis is introduced at 12 through a rotameter. At steady state, the mass in loop 9 consists mostly of intermediate 2-perfluoroalkylethyl sulfate and 2-perfluoroalkylethyl alcohol, the desired product, in about 18 to 22% sulfuric acid. Again, by adding the sulfur trioxide-rich mass from loop 3 into the zone of intense agitation at the impeller of centrifugal pump 10 in loop 9, it is quickly incorporated into the rapidly recirculating mass without the undesirable effects associated with the batch processes, run either at atmospheric pressure or above. The pressure in loop 9 is controlled by pressure relief device 13 through which the reaction mass in loop 9 is transferred to separating tank 14 which is held at about 95° C. for about 45 minutes to complete the hydrolysis of the remaining 2-perfluoro alkylethyl sulfate to 2-perfluoroalkylethyl alcohol which is rapid, and to allow the alcohol to settle cleanly. The separator 14 is operated at atmospheric pressure. Insoluble liquid 2-perfluoroalkylethyl alcohol is removed from the bottom of the separator and 2 to 4% hydrogen iodide solution is drawn from the side for recovery of the iodine value.

The 2-perfluoroalkylethyl iodides used in this invention may contain up to about twenty two carbon atoms as long as they can be introduced into the reaction zone as liquids. Mixtures of 2-perfluoro alkylethyl iodides of varying chain lengths are preferred because of their moderate melting points and ease and cost of procurement. Most preferred are mixtures containing chain lengths predominently in the C6 to C12 range. These mixtures are liquids at about 45° C. and the properties of their derivatives behave well in various applications. The 65% oleum used is normal commercial grade. There are no special purity requirements for the water used for the hydrolysis.

At steady state, the molar ratio of sulfur trioxide being fed to sulfation loop 3 as 65% oleum, to 2-perfluoroalkylethyl iodide being fed to the same loop, may range from about 6 to 1 to about 15 to 1. While the theoretical amount of sulfur trioxide to 2-perfluoroalkylethyl iodide is only 1.5 to 1, a ratio of about 6 to 1 is required to maintain reasonable fluidity in the system. The preferred range is 10+2 to 1. Ratios above 15 to 1 may be used but cost effectiveness suffers proportionally.

At steady state, sulfation loop 3 is operated to dissolve and react the 2-perfluoroalkylethyl iodides rapidly in the oleum in a zone of intense agitation at controlled temperatures and pressures. It should have an energy input of at least 0.05 horsepower per gallon per minute, preferably 0.5. The recycle time, i.e., the time to accomplish one complete recirculation of the entire contents of the loop, should be about 5 seconds or less, preferably 2 seconds or less. Residence times in the sulfation loop may vary. Generally they are one to two minutes. Higher residence times are undesirable because they require larger loop volumes with correspondingly higher pump capacities. Temperatures may range from about 40° C. to about 80° C. Temperatures of 65° to 75° C. are preferred because conversions are higher than at lower temperatures. At lower temperatures, the by-product bis-sulfate is less soluble and less reactive with $SO_3$, thereby reducing the rate of conversion to the desired end-product. In addition, at 65° and 75° C. (versus higher temperatures), excessive pressures are not required to maintain the sulfur trioxide and by-product sulfur dioxide in solution. Moreover, at temperatures of 65° to 75° C., pressures of 20 to 35 psig are sufficient to prevent undesireable foaming in loop 3. Temperatures of 65° to 75° C. in loop 3 may be attained by feeding the oleum at ambient temperature and by feeding the 2-perfluoroalkylethyl iodide at 50° to 80° C., no heating or cooling being required on the loop itself. The ratio of recycle to feeds in loop 3 should be 2 to 1 or higher.

At steady state, hydrolysis loop 9 is operated at a high degree of agitation to dissipate rapidly the instantaneous heat from the reaction of the excess oleum and the sulfate anhydride with water at suitable temperatures and pressures. The intense agitation also prevents the precipitated 2-perfluoroalkylethyl alcohol from coating unreacted intermediate 2-perfluoroalkylethyl sulfate and hindering its reaction to form product alchcol (see equation 6). This loop should have an energy input of at least 0.4 horsepower per gallon per minute with a recycle time of about 2 seconds or less. The loop is preferably run at temperatures of either above 95° C. or below 80° C., with temperatures of 70° to 80° C. most preferred, because of the tendency of 2-perfluoroalkylethyl alcohol to form hydrate gels at temperatures between about 80° and 95° C. These gels are capable of plugging the loop. For this same reason, the hold-up time in loop 9 is also preferably limited to about ½ minute which is long enough to insure complete hydrolysis of the excess sulfur trioxide in the feed but is short enough to prevent complete conversion of the 2-perfluoroalkyl ethyl pyrosulfate to 2-perfluoroalkylethyl alcohol with its potential for gel formation, should the temperature inadvertently move into the 80° to 95° C. range. The volume ratio of recycle to feeds in loop 9 should be above about 5 to 1 to minimize damage to the pump from the highly exothermic reactions of the sulfur trioxide and the 2-perfluoroalkylethyl pyrosulfate with water (feeds may be pulsating; 5:1 is an average). The preferred range is 10±2 to 1, at which ratios the reactions are completely under control. Ratios higher than the latter cause unnecessary reduction in volumetric efficiency and loss of capacity. Loop 9 is preferably maintained under 3 to 5 psig pressure. Higher pressures are also acceptable.

It should be noted that, while a centifugal pump was selected for generating both high liquid shear and rapid transport, other equipment or combinations of equipment which accomplish the same effects, would also be useful in our invention. For example, loops containing a gear pump for rapid transport in series with a rotating in-line mixer capable of furnishing high shear, in which mixer the feed stream could be introduced into the recirculating mass, would be effective.

EQUIPMENT DETAIL

In the pilot unit used to demonstrate this invention in the illustrative Examples which follow, the following equipment was used:

pumps 1 and 2 were Pulsa Series Diaphram Metering Pumps, Model 680-SE, by Pulsafeeder.

centrifugal pump 4 was a Model TE-5S-MD, 316SS centrifugal pump with magnetic drive made by March Manufacturing Inc. The impeller tips were trimmed of 6 mm of their length so as to adapt to the higher density (1.8 g/cc) of the oleum/2-perfluoroalkylethyl iodide reaction mass.

Teflon ® tubings 5 and 11 were both a nominal half inch in diameter (outside diameter of 12 mm, inside diameter of 9.5 mm) and 2 feet in length. All other lines shown in FIG. 1 were Teflon ®, a nominal quarter inch in diameter (outside diameter of 7 mm, inside diameter of 3 mm).

Pressure relief devices 7 and 13 were Series 975 Back Pressure Regulators by Mace Corporation.

Pump 10 was a Model MDX-MT3, centrifugal pump of Ryton plastic with magnetic drive, by March Manufacturing Inc.

Separator 14 was a 5-liter glass flask.

EQUIPMENT CHARACTERIZATION AND SAFETY

The locations of the feeds of 65% oleum into loop 3, and of the sulfonation mass which contains excess sulfur trioxide, into loop 9, warrant special attention which can be dealt with by careful routine experimentation. Severe safety problems and/or damage to the equipment, may be encountered if proper care is not taken or if proper pre-run equipment characterization is not carried out. If either of these feeds is injected too close to the impeller of pumps 4 and 10 respectively, some of the sulfur trioxide contained in each of these streams will vaporize and sear the impeller before the sulfur trioxide is absorbed into the system. If either is too far back in the loop, reaction will take place in the loop itself without the full effect of the intense zone of agitation at the impeller. Heat-searing will then be observed and heard on the tube wall. For example, it was found best to inject both the oleum and sulfonation mass feeds about one inch in front of the center of the pump impellers, in our pilot unit. A distance of one-half inch was found to be too close; a distance of one and one-half inches was too far. These distances may vary with pump size and should be determined by cautious experimentation using initially low oleum feed rates, before starting an actual synthesis. Of the two, the optimum location of the feed into pump 10 is more critical and should be determined with greater care.

It should also be noted that, because of the configuration of the feed port of pump 10, a March Model MDX-MT3, the feed line from loop 3 is optimally placed when it concentrically extends part way into the entry port of the pump.

The selection of the nominal half inch recycle tubing and the nominal quarter inch feed and transfer tubing size 5 and 11 was not arbitrary. Since the recycle rates are high and the feeds relatively low, it is important to size the recycle tubing and the feed and transfer tubing appropriately in keeping with good engineering practice.

The ammeters, 15 and 16, should be monitored during both characterization and synthesis runs, as they respond instantly to changes in liquid density and to problems in the recycle loops, such as a a frozen impeller drive, a broken impeller, power failure or air bubbles in the loop, thus affording quick insights into possible problems.

The back pressure regulators, 7 and 13, are critical safety features. The elements of "motorboating", a term known to those versed in the art of handling oleum, should be understood by those designing or operating equipment of the type described in this invention. The phenomenon of motorboating is described as the tendency of oleum to generate heat along its feed pipe when the pipe exit is in contact with water. This heat generates gaseous sulfur trioxide which expels the oleum from the line, and then sucks water back up the line. The heating, gasing and sucking cycle may repeat itself with the potential of drawing water back into the oleum feed reservoir. If this should occur, a reaction of explosive dimensions could easily result. The phenomenon of motorboating, as related to handling oleum, is generally accompanied by sounds generally associated with those of an operating motorboat. It is imperative that the back pressure regulators be in the system and in good working order.

As is well known to those skilled in the art of handling oleum, proper shielding of equipment to contain unexpected leakage and adequate protective clothing for operating personnel are mandatory, especially when the oleum is under pressure.

The large flow of recycle provided by the process of this invention dilutes incoming feeds and dissipates heat of reaction; the more exothermic the reaction, the more recycle liquid per volume of heat-generating feed. The liquid shear provided according to this invention makes for highly effective dissolution of solids and intimate mixtures of gases, solids and liquids (particularly highly viscous ones). In the sulfation reaction of the process of this invention, the centrifugal pump (or equivalent device) provides a backmixing function which disperses heat of reaction and presurizes by-product $SO_2$ so as to keep it in solution; horsepower and recycle are of secondary importance. In the hydrolysis reaction, horsepower and recycle are critical to the apparatus, because 65% oleum must be drowned in water during start-up and shutdown.

The following Examples are given by way of illustration, not limitation. In the Examples, the 2-perfluroalkylethyl iodide mixture was made up of those in which the perfluoroalkyl radicals contained the following percentages of carbon chain lengths:

$C_4 = 2\%$ $C_6 = 45\%$ $C_8 = 34\%$ $C_{10+} = 19\%$

EXAMPLE 1

The following was a typical run in the apparatus described above and shown in FIG. 1 (the sulfator and hydrolyzor were operated respectively at 0.7 HP/gal/min and 1.0 HP/gal/min with recycle times of 2 sec, with 2 ft. loops in both). Water at ambient temperature was added via 12 to hydrolyzer loop 9 at 680 ml/min and hydrolyzer pump 10 was turned on. With the pressure regulators 7 and 10 set at 20 psig and 3 psig respectively, the sulfator loop 3 was filled slowly with 65% oleum using pump 1 so that entrapped air would be at a minimum in the loop when pump 4 was turned on. When loop 3 was filled, the setting on pump 1 was raised to deliver about 160 g/min of 65% oleum. Pump 4 was then turned on. When oleum was flowing through sulfator loop 3 and drowning into water without incident in hydrolyzer loop 9, the feed of 2-perfluoroalkylethyl iodide mixture was begun by turning on pump 2 at a low setting. The goal feed rate of 80 g/min was approached by slowly increasing the pumping speed over about 1 to 2 minutes. This was done so that the oleum feed rate to hydrolyzer loop 9 would not be increased at too rapid a rate.

The two loop reactor system was then run feeding 65% oleum at 160 g (1.3 mol of sulfur trioxide)/min and 98.6% pure 2-perfluoroalkylethyl iodides at 80 g(0.13 mol)/min to sulfator loop 3 and water at 640 g/min to hydrolyzer loop 9. The molar ratio of sulfur trioxide to 2-perfluoroalkylethyl iodides was therefore 10.1 to 1. Feed temperature for the oleum ranged between 15° and 20° C. Feed temperature of the 2-perfluoroalkylethyl iodides was 50° to 60° C. Water temperature was 18° C. Loop 3 ran at about 54° C. and loop 9 at about 75° C. Neither loop was heated or cooled. The temperature in separater 14 was maintained at 95° C. by means of external heating. Product 2-perfluoroalkylethyl alcohol mixture was obtained at the rate of 64 g/min. Analysis by gas chromatography showed a purity of 94.8% indicating a yield of 0.12 mol/min or 96+% of theory. The product also contained 1.7% 2-perfluoroalkylethyl ethers (see equation 9), 1.1% 2-perfluoroalkylethyl-bis-sulfates (equation 3) and 1.9% 2-perfluoroalkylethyl iodides (believed to have been formed according to equation 10 rather than being unreacted starting material). Treatment of the hydrogen iodide liquor, drawn from the top of the separator, with 30% hydrogen peroxide resulted in the recovery of 92% of the iodine value, charged to the system as 2-perfluoroalkylethyl iodide, as molecular iodine.

The reactor system was shut down by first turning off 2-perfluoroalkylethyl iodide pump 2, thus allowing the 65% oleum feed to flush out the loop. The 65% oleum was, in turn, flushed out of the system with 2 to 5% oleum. Flushes with 98% sulfuric acid, 70% sulfuric acid and finally water followed. Hydrolyzer loop 9 was allowed to self-flush with water which was the last feed stream shut off.

EXAMPLE 2

Example 2 was run similarly to Example 1 with the exception that the feed temperature of the 2-perfluoroalkylethyl iodide mixture was adjusted to 80° to 90° C. instead of 50° to 60° C. This resulted in loop 3 running at about 65° C. At steady state, the product 2-perfluoroalkylethyl alcohol mixture was 97% pure.

I claim:

1. In a process for the manufacture of 2-perfluoroalkylethyl alcohols by reacting 2-perfluoroalkylethyl iodides with oleum followed by hydrolysis of the resulting sulfated reaction mass with water, the improvement comprising continuously feeding oleum to a reaction mass contaning said iodides, and continuously feeding a portion of the resulting sulfated reaction mass to a reaction mass containing water, carrying out both reactions in two similar continuous reactor systems, combined in series, in each of which said reactant feed stream is contacted with said reaction mass in a zone of intense agitation which forms part of a low volume recycle loop operated under pressure and at high rates of recycle, wherein:

said zone of intense agitation in said sulfation loop has an energy input of at least 0.05 horsepower per gallon per minute with a loop recycle time of 5 seconds or less;

said zone of intense agitation in said hydrolysis loop has an energy input of at least 0.4 horsepower per gallon per minute with a loop recycle time of 2 seconds or less, and in which sufficient presure is maintained in said sulfation and hydrolysis loops to suppress foaming.

2. The process of claim 1 wherein the energy input to the liquids in both loops is provided by centrifugal pumps.

3. The process of claim 1 wherein the ratio of (i) the volume of material being recycled in the hydrolysis loop to (ii) the volume of material being fed to the hydrolysis loop from the sulfation loop is at least 5 to 1.

4. The process of claim 3 wherein said ratio is 10±2 to 1.

* * * * *